US009241477B2

(12) United States Patent
Mukaddam et al.

(10) Patent No.: US 9,241,477 B2
(45) Date of Patent: Jan. 26, 2016

(54) FLUID DELIVERY SYSTEM, AND ASSOCIATED APPARATUS AND METHOD

(71) Applicant: FORMULATRIX, INC., Waltham, MA (US)

(72) Inventors: Kabir Mukaddam, Cambridge, MA (US); Pratomo Alimsijah, Allston, MA (US)

(73) Assignee: FORMULATRIX, INC., Waltham, ME (US)

( * ) Notice: Subject to any disclaimer, the term of this patent is extended or adjusted under 35 U.S.C. 154(b) by 101 days.

(21) Appl. No.: 13/942,737

(22) Filed: Jul. 16, 2013

(65) Prior Publication Data

US 2014/0014040 A1    Jan. 16, 2014

Related U.S. Application Data

(60) Provisional application No. 61/672,018, filed on Jul. 16, 2012.

(51) Int. Cl.
*A01K 45/00* (2006.01)
*G01N 21/53* (2006.01)

(52) U.S. Cl.
CPC ............ *A01K 45/007* (2013.01); *G01N 21/534* (2013.01); *Y10T 137/0318* (2015.04); *Y10T 137/86027* (2015.04)

(58) Field of Classification Search
CPC ..... A01K 45/007; A01K 43/00; A01K 67/02; G01N 21/49; G01N 21/534; G01N 29/4445; C02F 2103/20
USPC .......................................................... 119/6.8
See application file for complete search history.

(56) References Cited

U.S. PATENT DOCUMENTS

| 5,493,994 | A | * | 2/1996 | Cox | ........................ | A01K 41/00 119/174 |
| 5,900,929 | A | | 5/1999 | Hebrank et al. | | |
| 5,967,080 | A | * | 10/1999 | Cox | ..................... | A01K 45/007 119/6.8 |
| 6,240,877 | B1 | * | 6/2001 | Bounds | .......................... | 119/6.8 |
| 6,286,455 | B1 | * | 9/2001 | Williams | ............. | A01K 45/007 119/6.8 |
| 6,668,753 | B2 | | 12/2003 | Hebrank | | |
| 7,096,820 | B2 | | 8/2006 | Correa et al. | | |
| 8,016,260 | B2 | | 9/2011 | Mukaddam et al. | | |

(Continued)

OTHER PUBLICATIONS

KIPO, International Search Report and Written Opinion mailed Oct. 18, 2013, for corresponding international application PCT/US13/50585 filed Jul. 16, 2013.

*Primary Examiner* — Monica Williams
*Assistant Examiner* — George Andonyan
(74) *Attorney, Agent, or Firm* — Olive Law Group, PLLC

(57) ABSTRACT

A fluid delivery system for an in ovo injection apparatus is provided. Such a fluid delivery system includes a plurality of fluid pumps each having a select valve, a diaphragm valve, and an outlet valve. The select valves are individually controllable such that each select valve is selectively operated via a pneumatic actuator. The diaphragm valves and the outlet valves are commonly operated via respective pneumatic actuators. An input valve is provided for each fluid pump in instances that require high pressure delivery of a fluid substance via the fluid pumps. In such instances, the input valves and the diaphragm valves are commonly controlled via high pressure solenoid valves, while the select valves are selectively controlled and the outlet valves are commonly controlled via low pressure solenoid valves. An associated apparatus and method are also provided.

3 Claims, 15 Drawing Sheets

(56) References Cited

U.S. PATENT DOCUMENTS

| | | |
|---|---|---|
| 8,100,293 B2 | 1/2012 | Mukaddam et al. |
| 2003/0056729 A1* | 3/2003 | Correa et al. ................ 119/6.8 |
| 2003/0150387 A1* | 8/2003 | Hebrank ...................... 119/6.8 |
| 2005/0039688 A1 | 2/2005 | Correa et al. |
| 2006/0144252 A1 | 7/2006 | Loflink, Jr. et al. |
| 2007/0044721 A1 | 3/2007 | Ilich |
| 2012/0017835 A1 | 1/2012 | Nadreau et al. |

* cited by examiner

FLUID DELIVERY SYSTEM, AND ASSOCIATED APPARATUS AND METHOD

CROSS REFERENCE TO RELATED APPLICATIONS

This application claims priority to U.S. Provisional Patent Application No. 61/672,018 filed on Jul. 16, 2012, the entire contents of which are hereby incorporated by reference herein.

TECHNICAL FIELD

The present disclosure generally relates to fluid delivery systems. More particularly, the present disclosure relates to a fluid delivery system implemented on an in ovo injection apparatus, and an associated method.

BACKGROUND

In many instances, it is desirable to introduce a substance into a live avian egg prior to hatch. Injections of various substances into avian eggs is commonly referred to as in ovo injection. Such injections have been employed to decrease post-hatch mortality rates, increase the potential growth rates or eventual size of the resulting bird, and even to influence the gender determination of the embryo. Similarly, injections of antigens into live eggs have been employed to incubate various substances used in vaccines which have human or animal medicinal or diagnostic applications. Examples of substances that have been used for, or proposed for, in ovo injection include vaccines, antibiotics and vitamins. In addition, removal of material from avian eggs has been employed for various purposes, such as testing and vaccine harvesting.

An egg injection apparatus (i.e., in ovo injection apparatus) may comprise a plurality of injection devices which operate simultaneously or sequentially to inject a plurality of eggs. The injection apparatus may comprise an injection head which comprises the injection devices, and wherein each injection device is in fluid communication with a source containing a treatment substance to be injected. The in ovo injection apparatus conventionally is designed to operate in conjunction with commercial egg carrier carriers or flats. Egg flats utilized in conjunction with an in ovo injection apparatus typically contain an array of pockets that are configured to support a respective plurality of avian eggs in a generally upright orientation. The egg flats may be typically transported through the in ovo injection apparatus via an automated conveyor system for registering the egg flat beneath the injection head for injection of the eggs carried by the egg flat. In ovo injection of substances (as well as in ovo extraction of materials) typically occurs by piercing an egg shell to form an opening (e.g., via a punch), extending an injection needle through the hole and into the interior of the egg (and in some cases into the avian embryo contained therein), and injecting treatment substance(s) through the needle and/or removing material therefrom.

In some instances, in ovo injection may be implemented selectively such that the treatment substance is not dispensed into dead, infertile, or missing eggs. In this regard, a candling device may be used to classify the eggs in the egg flat conveyed through the egg injection apparatus as viable or nonviable. In some instances, the classification information may be transmitted to an egg remover for removal of the non-viable eggs such that only viable eggs are conveyed to the injection devices, and then the classification information is transmitted to the injection devices such that the treatment substance is only dispensed at locations where eggs (viable) are present. In other instances, the classification information may be transmitted directly to the injection devices such that the viable eggs are injected with the treatment substance, while the non-viable eggs are not injected therewith. Either of these manners of using classification information is typically referred to as selective injection.

The treatment substances used in ovo may typically be either oil-based or aqueous-based substances. Delivery of aqueous-based substances is accomplished using low pressure (typically less than about 30 psi (206 KPa)) to inject the eggs, while delivery of oil-based substances requires use of high pressure (typically more than about 200 psi (1378 KPa)) due to the viscosity difference over aqueous-based substances. Selective injection of aqueous-based substances is accomplished using low pressure solenoid valves in fluid communication with each injection device such that dispensing of the treatment substance can be individually controlled for each injection device. However, selective injection of oil-based substances would require high pressure solenoid valves, which are expensive compared to low pressure solenoid valves, for each injection device to provide individual control thereof.

Accordingly, it would be desirable to provide a fluid delivery system for implementation on an in ovo injection apparatus capable of providing selective delivery of oil-based treatment substances, without the need for every injection device to be in communication with a high pressure solenoid for facilitating individual control thereof. Furthermore, it would be desirable to provide an associated method that would facilitate selective injection of an oil-based treatment substance at high pressure without the need for high pressure solenoid valves in communication with each injection device.

BRIEF SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

According to one aspect, a fluid delivery system is provided. The system includes a plurality of fluid pumps adapted for fluid communication with a fluid reservoir. Each fluid pump includes a fluid channel configured to receive a fluid substance from the fluid reservoir, a select valve disposed along the fluid channel and being individually controllable, an outlet valve disposed along the fluid channel downstream from the select valve, a diaphragm valve disposed along the fluid channel between the select valve and the outlet valve, and an input valve disposed along the fluid channel between the select valve and the diaphragm valve. The system further includes a plurality of select valve actuators in fluid communication with the select valves for individual pneumatic control thereof, an outlet valve actuator in fluid communication with the outlet valves for commonly controlling pneumatic operation thereof, a diaphragm actuator in fluid communication with the diaphragm valves for commonly controlling pneumatic operation thereof, and an input valve actuator in fluid communication with the input valves for commonly controlling pneumatic operation thereof.

According to one aspect, the system includes a dispensing device in fluid communication with the fluid channel downstream from the outlet valve.

According to one aspect, the select valve actuators, the outlet valve actuator, the diaphragm actuator, and the input valve actuator are configured to control their respective valves by switching between positive air pressure and vacuum.

According to one aspect, the select valve actuators and the outlet valve actuator are configured to pneumatically control the select valves and the outlet valves at low pressure. The input valve actuator and the diaphragm actuator are configured to pneumatically control the input valves and diaphragm valves at high pressure.

According to one aspect, the select valve actuators and the outlet valve actuator are configured to pneumatically control the select valves and the outlet valves at less than about 30 psi (206 KPa). The input valve actuator and the diaphragm actuator are configured to pneumatically control the input valves and diaphragm valves at more than about 200 psi (1378 KPa).

According to one aspect, the select valve actuators and the outlet valve actuator are low pressure solenoid actuators. The input valve actuator and the diaphragm actuator are high pressure solenoid actuators.

According to one aspect, a method for delivering a fluid to a plurality of dispensing locations is provided. The method includes applying positive air pressure to each of a select valve, an input valve, a diaphragm valve, and an outlet valve of a plurality of fluid pumps, selectively applying vacuum to the select valves so as to selectively allow a fluid substance to flow along a plurality of fluid channels from a fluid reservoir, commonly applying vacuum to the input valves, commonly applying vacuum to the diaphragm valves so as to advance the fluid substance along the fluid channels from the select valves being selectively operated, selectively applying positive air pressure to the select valves, commonly applying positive air pressure to the input valves, commonly applying vacuum to the outlet valves so as to allow the fluid substance to advance along the fluid channel from the diaphragm valve for more than one of the fluid pumps, and commonly applying positive air pressure to the diaphragm valves so as to advance the fluid substance along the fluid channel from the outlet valve for more than one of the fluid pumps.

According to one aspect, applying positive air pressure to each of a select valve, an input valve, a diaphragm valve, and an outlet valve of a plurality of fluid pumps includes commonly applying positive air pressure to the input valves, the diaphragm valves, and the outlet valves.

According to one aspect, commonly applying positive and vacuum to the input valves and the diaphragm valves is facilitated by respective high pressure solenoid valves. Commonly applying positive and vacuum to the outlet valves and selectively applying positive and vacuum to the select valves are facilitated by respective low pressure solenoid valves.

According to one aspect, the high pressure solenoid valves control the input valves and the diaphragm valves at more than about 200 psi (1378 KPa), and the low pressure solenoid valves control the outlet valves and the select valves at less than about 30 psi (206 KPa).

According to one aspect, the method includes advancing the fluid substance along the fluid channel from the outlet valve to an injection device, and injecting the fluid substance into an avian egg.

According to one aspect, an in ovo injection apparatus capable of injecting a plurality of avian eggs carried by an egg carrier is provided. The apparatus includes a fluid delivery system for delivering a treatment substance to an avian egg. The fluid delivery system includes at least one manifold having a plurality of fluid pumps configured for fluid communication with a fluid reservoir. Each fluid pump includes a fluid channel configured to receive a fluid substance from the fluid reservoir, a select valve disposed along the fluid channel and being individually controllable, an outlet valve disposed along the fluid channel downstream from the select valve, a diaphragm valve disposed along the fluid channel between the select valve and the outlet valve, and an input valve disposed along the fluid channel between the select valve and the diaphragm valve. The fluid pump further includes a plurality of select valve actuators in fluid communication with the select valves for individual pneumatic control thereof, an outlet valve actuator in fluid communication with the outlet valves for commonly controlling pneumatic operation thereof, a diaphragm actuator in fluid communication with the diaphragm valves for commonly controlling pneumatic operation thereof, and an input valve actuator in fluid communication with the input valves for commonly controlling pneumatic operation thereof. The fluid delivery system further includes an injection assembly in fluid communication with the fluid delivery system, the injection assembly having a plurality of injection devices. Each injection device is in fluid communication with a respective fluid pump and configured to inject a respective avian egg when aligned therewith.

According to one aspect, a fluid pump assembly is provided. The fluid pump assembly includes a fluid pump in communication with a fluid reservoir. The fluid pump includes a first panel defining a fluid channel configured to receive a fluid substance from the fluid reservoir and a second panel spaced-apart and opposing the first panel and defining a chamber therebetween. The second panel defines a select valve channel extending into the chamber and configured for supplying a pressure source thereto, an outlet valve channel downstream from the select valve channel and extending into the chamber and configured for supplying a pressure source thereto, a diaphragm valve channel between the select valve channel and the outlet valve channel and extending into the chamber and configured for supplying a pressure source thereto, and an input valve channel between the select valve portion and the diaphragm valve portion and extending into the chamber and configured for supplying a pressure source thereto. A resilient membrane is provided in the chamber and in communication with the channel for directing flow of fluid therethrough. The resilient membrane includes a select valve portion being individually controllable, an outlet valve portion, a diaphragm valve portion, and an input valve portion. The fluid pump assembly further includes a select valve actuator in fluid communication with the select valve channel for control of the select valve portion, an outlet valve actuator in fluid communication with the outlet valve channel for control of the outlet valve portion, a diaphragm actuator in fluid communication with the diaphragm valve channel for control of the diaphragm valve portion, and an input valve actuator in fluid communication with the input valve channel for control of the input valve portion.

According to one aspect, a fluid pump is provided. The pump includes a first panel that defines a fluid channel configured to receive a fluid substance from the fluid reservoir and a second panel spaced-apart and opposing the first panel and defining a chamber therebetween. A select valve channel extends into the chamber and is configured for supplying a pressure source thereto and an outlet valve channel is provided downstream from the select valve channel and extends into the chamber and is configured for supplying a pressure source thereto. A resilient membrane is configured for being received in the chamber and is in communication with the channel for directing flow of fluid therethrough. The resilient membrane defines a select valve portion being individually controllable and an outlet valve portion. A select valve actuator is in fluid communication with the select valve channel for control of the select valve portion and an outlet valve actuator is in fluid communication with the outlet valve channel for control of the outlet valve portion.

BRIEF DESCRIPTION OF THE DRAWINGS

Figure 1:
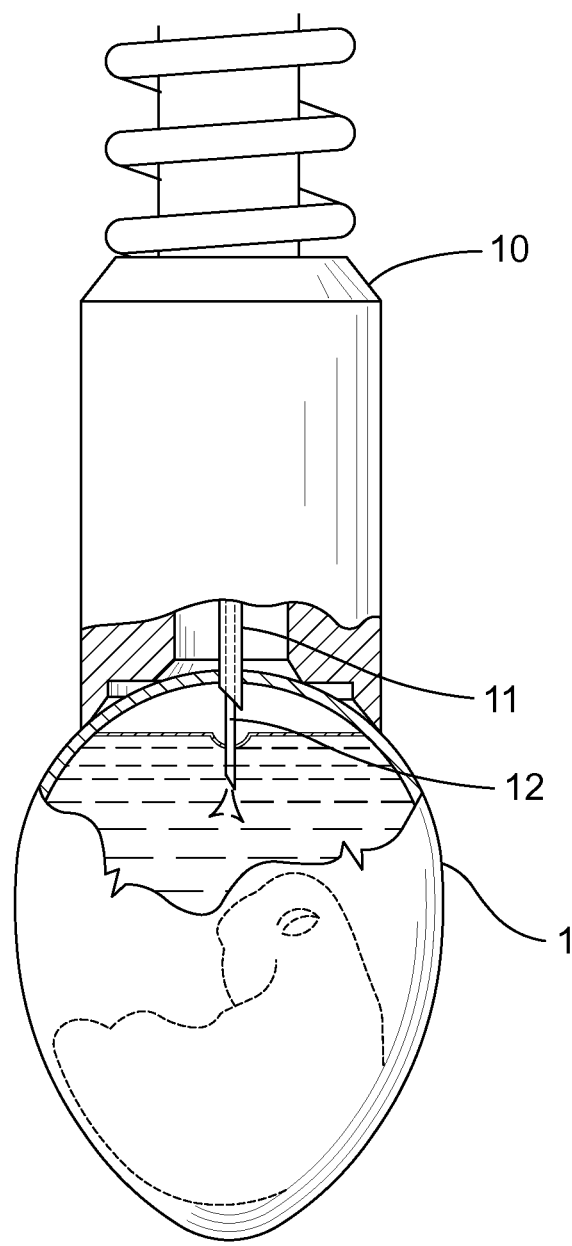
Figure 2:
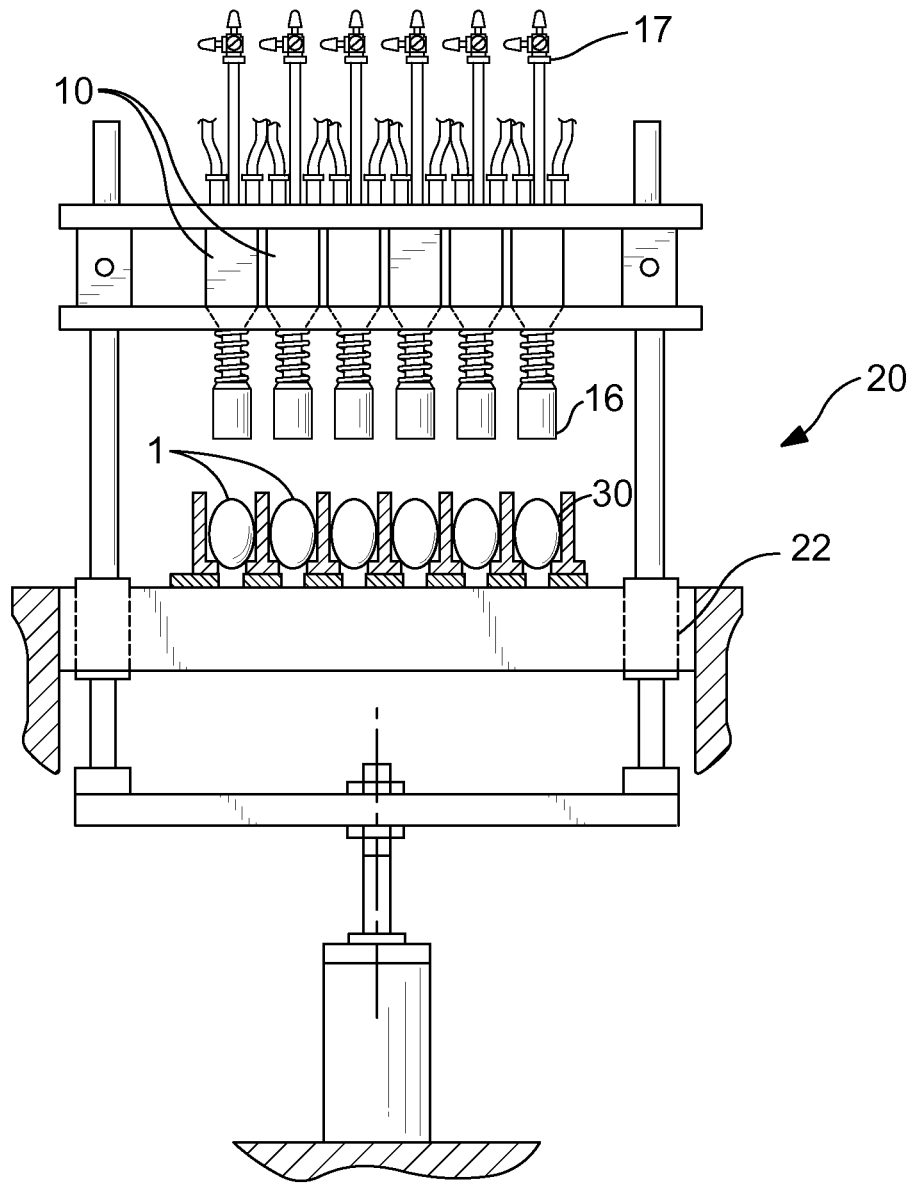
Figure 3:
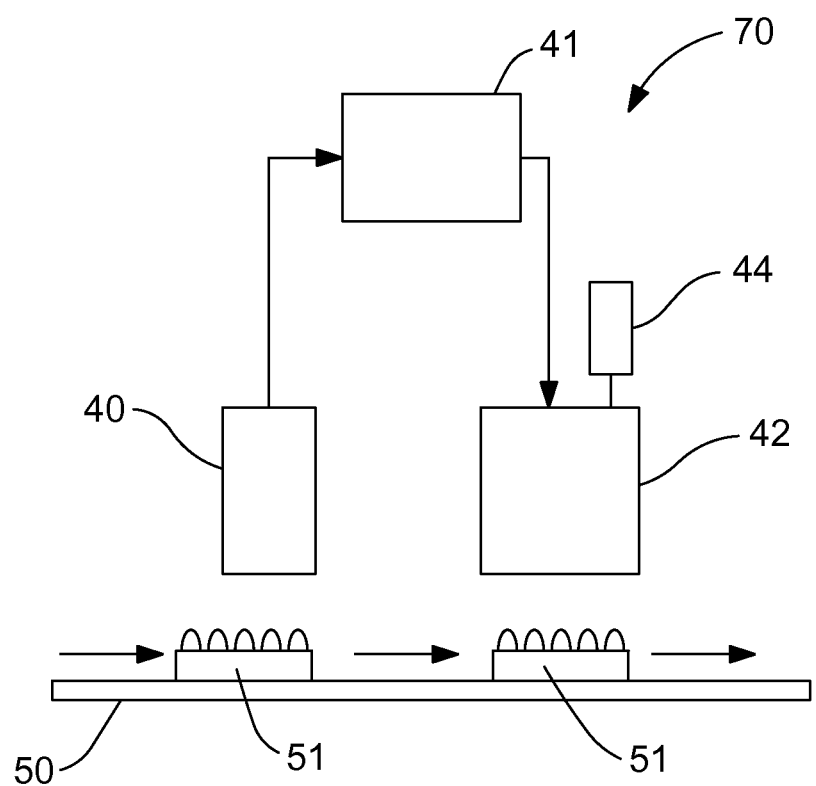
Figure 4:
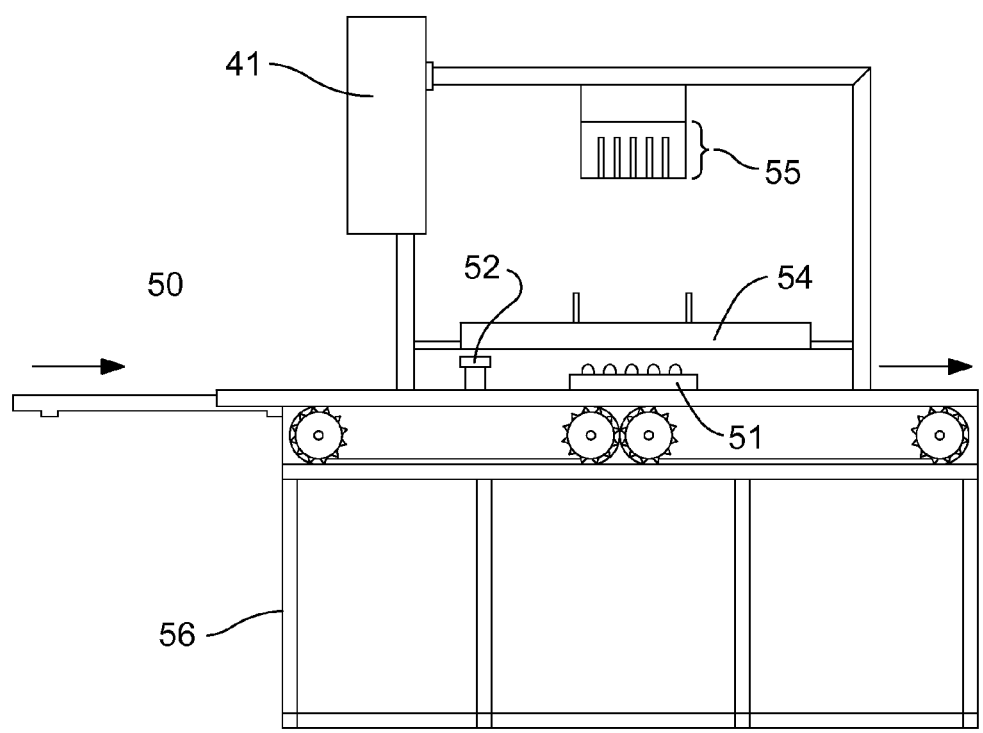
Figure 5:
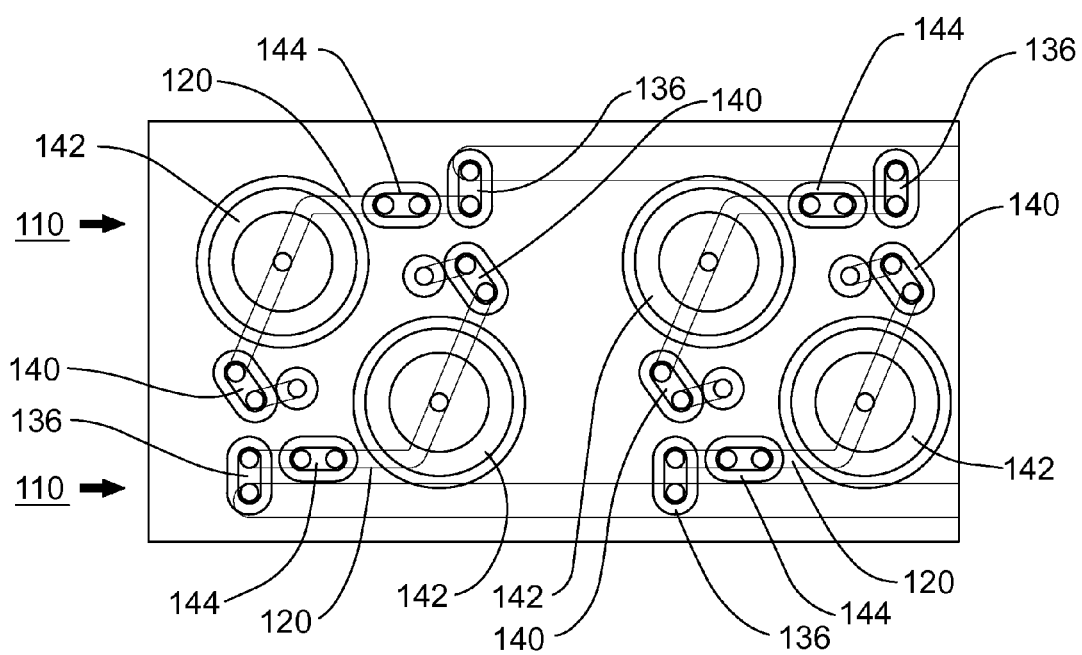
Figure 13:
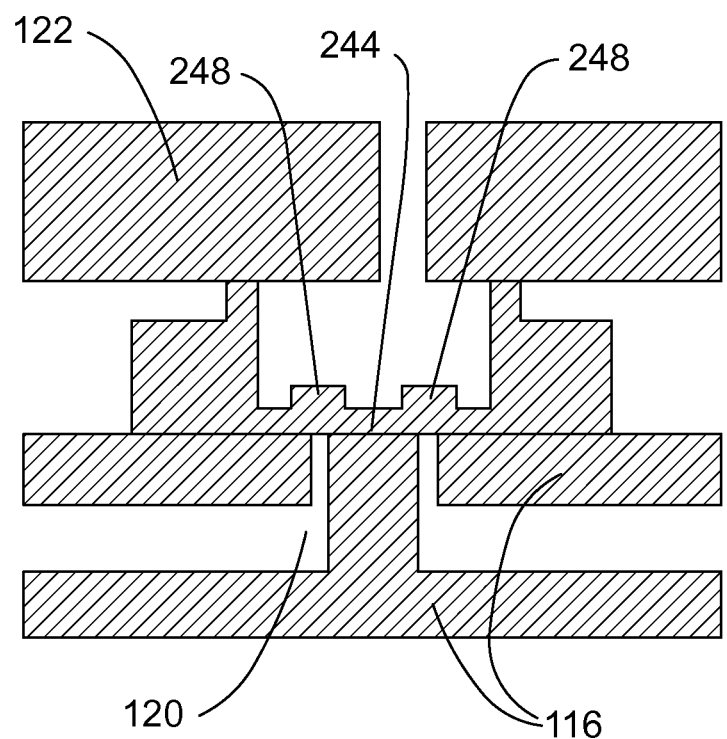
Figure 14:
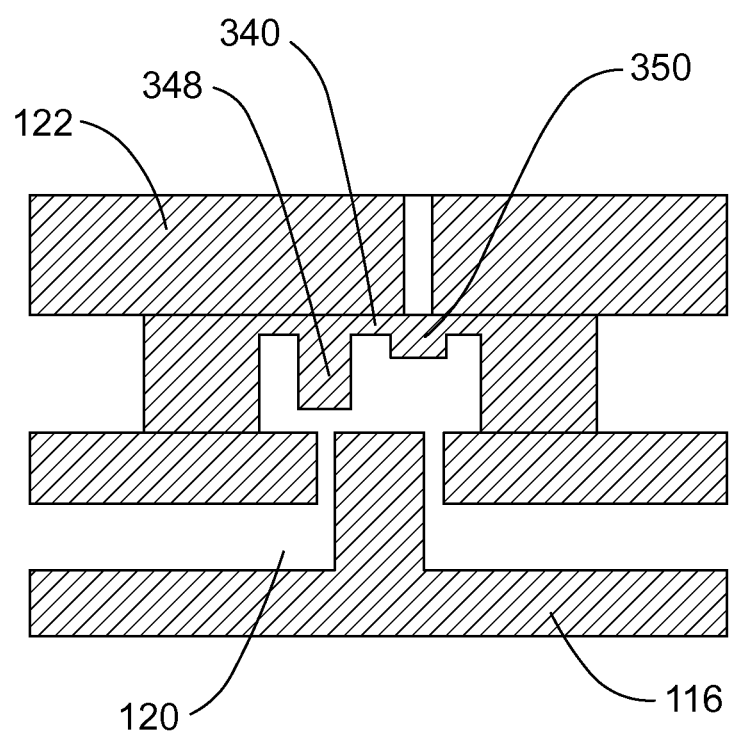
Figure 15:
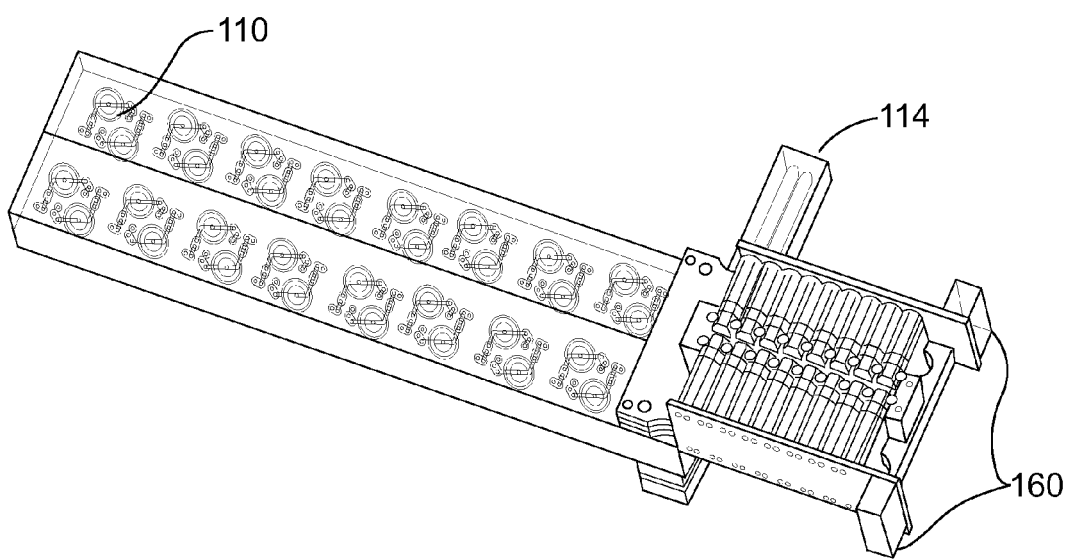

Having thus described various embodiments of the present disclosure in general terms, reference will now be made to the accompanying drawings, which are not necessarily drawn to scale, and wherein:

FIG. 1 is a partial cross-sectional view of an in ovo injection delivery device capable of delivering a treatment substance into an avian egg, according to one aspect of the present disclosure;

FIG. 2 is a side view of an in ovo injection apparatus having a plurality of injection devices capable of delivering a treatment substance into a plurality of avian eggs, according to one aspect of the present disclosure;

FIG. 3 is a schematic view of a selective injection device, according to one aspect of the present disclosure;

FIG. 4 is a side view of the selective injection device of FIG. 3;

FIG. 5 is a top view of a fluid pump for use with an in ovo injection apparatus;

FIGS. 6 through 12 represent operational sequential views of a schematic cross-section view of a fluid pump capable of use with an in ovo injection apparatus for selectively delivering a fluid substance at a high pressure according to one aspect of the present disclosure;

FIG. 13 is a schematic cross-section view of a valve portion for use with a fluid pump provided herein according to one aspect of the present disclosure;

FIG. 14 is a schematic cross-section view a valve portion for use with a fluid pump provided herein according to one aspect of the present disclosure; and FIG. 15 is a perspective view of a fluid dispensing system according to one aspect of the present disclosure.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

An exemplary in ovo processing system that may be utilized to inject a substance, particularly substances such as oil-based and aqueous-based treatment substances, into eggs in accordance with aspects of the present disclosure, is the INOVOJECT® automated injection device (Embrex, Inc., Durham, N.C.). However, embodiments of the present invention may be utilized with any in ovo processing device.

FIG. 1 illustrates a portion of an injection delivery device 10 of the INOVOJECT® automated injection device. The injection delivery device 10 includes a punch 11 configured to form an opening in the shell of an egg 1. An injection needle 12 is movably disposed within the punch 11 (i.e., the punch 11 substantially concentrically surrounds the respective needle 12) so that after the punch 11 makes an opening in the shell of an egg, the injection needle 12 can move through the punch 11 and respective opening of an egg shell to an injecting position(s) within an egg for delivery of multiple substances therein. However, various types of injection delivery devices may be utilized in accordance with aspects of the present disclosure. Aspects of the present disclosure are not limited to the illustrated injection delivery device.

After injection of one or more substances into an egg via the injection delivery device 10 of FIG. 1, portions of the punch and needle 11, 12 are treated with a sanitizing fluid, for example, via spraying, dipping, and allowing sanitizing fluid to flow through the needle and/or punch, and the like.

FIG. 2 illustrates an in ovo injection apparatus 20 having a plurality of the injection delivery devices 10 of FIG. 1 that can be configured to inject one or more substances, particularly substances such as oil-based and/or aqueous-based substances, in multiple eggs according to aspects of the present disclosure. The illustrated apparatus 20 includes a stationary base 22, and a plurality of injection delivery devices 10. A flat 30 holds a plurality of eggs 1 in a substantially upright position. The flat 30 is configured to provide external access to predetermined areas of the eggs 1. Each egg 1 is held by the flat 30 so that a respective end thereof is in proper alignment relative to a corresponding one of the injection delivery devices 10 as the injection delivery device 10 advances towards the base 22 of the apparatus. However, in ovo injection devices may inject eggs oriented in various orientations. Aspects of the present disclosure are not limited only to in ovo injection devices that inject eggs in the illustrated orientation.

Each of the plurality of injection delivery devices 10 has opposing first and second ends 16, 17. The delivery devices 10 have a first extended position and a second retracted position. Upon extension of an injection delivery device 10, the first end 16 is configured to contact and rest against predetermined areas of an external egg shell. From this position, a punch 11 (FIG. 1) within the delivery device 10 forms a small opening in the shell and an injection needle 12 (FIG. 1) is inserted therethrough to deliver one or more substances into the egg. When not injecting, the injection delivery devices 10 are retracted to rest a predetermined distance above the eggs 1 and stationary base 22. Alternatively, the base 22 can be longitudinally slidably moveable to position the eggs 1 in proper position relative to the injection heads 10.

Each delivery device 10 may be configured to deliver discrete amounts of a treatment substance. The apparatus includes a fluid delivery system 50 that pumps a treatment substance through the delivery devices 10. The fluid delivery system 50 includes a plurality of pumps in fluid communication with a fluid reservoir 54 and with each of the delivery devices 10. Pumps 52 in the fluid delivery system 50 may be arranged in a manifold in fluid communication with the fluid reservoir 54. Embodiments of the present invention are not limited to the illustrated configurations of a single fluid delivery system. For example, more than one substance reservoir may be utilized for each system. In this regard, a plurality of fluid delivery systems may be implemented to provide more than one treatment substances. In some instances, each pump may be used to deliver more than one treatment substance to the delivery devices.

One aspect of the present disclosure combines an automated in ovo injection device with an apparatus for classifying each egg in a plurality of avian eggs as either suitable for injection or not suitable for injection. The classification device (or "classifier") is operatively associated with the injection device, so that only those eggs identified as suitable for injection are injected with a treatment substance.

The classification of eggs as suitable for injection (or "suitable") may be based on the identification of eggs as either fertile or non-fertile, with fertile eggs being suitable for injection. Alternatively, the classification may be based on the identification of eggs as either live (i.e., eggs that contain a living embryo) or non-live (i.e., infertile or containing a dead embryo), with live eggs being suitable for injection. As used herein, the term "non-live" egg refers to an egg that has either not been fertilized or that was fertilized but in which the avian embryo has died. As used herein, the term "dead" egg refers to an egg that contains an avian embryo that has died. "Non-live" eggs thus include both non-fertile and dead eggs. Non-live eggs will not hatch. Additionally, the classification may be designed to identify "empty eggs" (in which the internal contents have leaked out) as well as "missing eggs" (where the egg compartment passing through the apparatus does not contain any egg). Empty and missing eggs are classified as not suitable for injection. Eggs identified as clear (infertile), dead and/or mid dead can be removed by any conventional method, including manually or by suction-type lifting devices.

Where classification is designed to distinguish infertile eggs ("clear eggs") from fertile eggs, and to classify fertile eggs as suitable for injection, it is recognized that eggs classified as fertile may include some dead eggs. The present methods of selectively injecting eggs identified as suitable for injection may equally well be described as a method of selectively not injecting eggs identified as unsuitable for injection, as will be apparent to one skilled in the art.

As used herein, the term "treatment substance" refers to a substance that is injected into an egg to achieve a desired result. Similarly, dosing or dosage may refer to one unit of a treatment substance, meaning one unit of a treatment substance for a respective egg. Treatment substances include but are not limited to vaccines, antibiotics, vitamins, virus, and immunomodulatory substances. Vaccines designed for in ovo use to combat outbreaks of avian diseases in the hatched birds are commercially available. Typically the treatment substance is dispersed in a fluid medium, e.g., is a fluid or emulsion, or is a solid dissolved in a fluid, or a particulate dispersed or suspended in a fluid.

As used herein, the term "needle" or "injection needle" refers to an instrument designed to be inserted into an egg to deliver a treatment substance into the interior of the egg. A number of suitable needle designs will be apparent to those skilled in the art. The term "injection tool" as used herein refers to a device designed to both pierce the shell of an avian egg and inject a treatment substance therein. Injection tools may comprise a punch for making a hole in the egg shell, and an injection needle that is inserted through the hole made by the punch to inject a treatment substance in ovo. Various designs of injection tools, punches, and injection needles will be apparent to those in the art.

As used herein, "in ovo injection" refers to the placing of a substance within an egg prior to hatch. The substance may be placed within an extraembryonic compartment of the egg (e.g., yolk sac, amnion, allantois) or within the embryo itself. The site into which injection is achieved will vary depending on the substance injected and the outcome desired, as will be apparent to those skilled in the art.

FIG. 3 schematically illustrates an apparatus 70 that can be used to carry out the selective injection methods of the present disclosure. In overview, with reference to FIG. 3, an apparatus 70 of the invention comprises: a classifier 40 for classifying eggs as either suitable for injection or as non-suitable for injection; a controller 41 for receiving signals from the classifier and for generating a selective injection signal based on the presence and relative position of each suitable egg; and an injector 42 associated with the controller for injecting only those eggs identified as suitable. The injector 42 comprises at least one reservoir 44 for holding the treatment substance to be injected into the eggs identified as suitable. A conveyor 50 is configured to move a plurality of eggs (for example, eggs contained in a commercial egg flat) past the classifier 40 and injector 42. The direction of travel of the eggs along the conveyors is indicated by arrows in FIG. 3.

As used herein, the "selective generation of an injection signal" (or the generation of a selective injection signal), refers to the generation by the controller of a signal that causes injection only of those eggs identified by the classifier as suitable for injection. As will be apparent to those skilled in the art, generation of a selective injection signal may be achieved by various approaches, including generating a signal that causes the injection of suitable eggs, or generating a signal that prevents the injection of non-suitable eggs.

A preferred injector for use in the methods described herein is the INOVOJECT® automated injection device (Embrex, Inc., Durham, N.C.). However, any in ovo injection device capable of being operably connected, as described herein, to manners for classifying eggs is suitable for use in the present methods. Suitable injection devices preferably are designed to operate in conjunction with commercial egg carrier devices or "flats", examples of which are described herein. Preferably, the eggs to be injected according to the present methods are carried in egg flats as described herein; however, as will be apparent to those skilled in the art, any manner of presenting a plurality of eggs over time to the classifier for identification of suitable eggs can be used in the present methods. The eggs may pass one at a time under the classifier or, as described herein, the classifier may be configured so that a number of eggs can pass under the classifier simultaneously.

Preferably, the injector comprises a plurality of injection needles, to increase the speed of operation. The injector may comprise a plurality of injection needles which operate simultaneously or sequentially to inject a plurality of eggs, or alternatively may comprise a single injection needle used to inject a plurality of eggs.

As shown in FIG. 4, the injection device may comprise an injection head 54 in which the injection needles (not shown) are situated. The injection head or the injection needles are capable of movement in order to inject eggs. Each injection needle is in fluid connection with a reservoir containing the treatment substance to be injected. A single reservoir may supply all of the injection needles in the injection head, or multiple reservoirs may be utilized. An exemplary injection head is shown in FIG. 2, where conveyor 50 has aligned egg flat 51 with the injection head 54. Each injection needle (not shown) is housed in a guiding tube designed to rest against the exterior of an egg. Each injection needle is operably connected to a fluid delivery system. Each fluid delivery system is in fluid connection with a reservoir (not shown) containing the treatment substance.

As shown in FIG. 3, eggs may be conveyed past the classifier 40 and the injector 42 in a fixed array (i.e., in a fixed position relative to other eggs), so that signals generated by the classifier, when conveyed to the injector, result in injection only of those eggs identified as suitable by the classifier. In other words, the eggs are prevented from changing their position relative to other eggs while passing from the classifier to the injector. This may be accomplished, for example, by utilizing commercial egg flats to transport a plurality of eggs along the conveyor.

A classifier for identifying eggs suitable for injection may utilize light that is pulsed or cycled at a frequency different from (and, in some instances, higher than) ambient light. However, those skilled in the art will appreciate that any automated method of distinguishing live from non-live eggs, or fertile from non-fertile eggs, and generating a signal to a controller for processing may be utilized. Methods of classifying eggs include those based on the temperature of the egg, or the quality or quantity of light that passes through an egg.

According to some aspects, the step of classifying eggs as suitable for injection is accomplished using a light measuring system, in which light is transmitted through an egg and assessed by a light detector. The eggs are identified as either fertile (suitable for injection) or non-fertile (not suitable for injection). The light detectors are operatively connected to a controller (which may be a microprocessor or other programmable or non-programmable circuitry). Manners for conveying a plurality of eggs past the light measuring system is situated so the each egg passes through the light measuring system and data is generated for each egg. The data collected by the light measuring system is provided to the controller for processing and storing data associated with each egg, and the controller generates a selective injection signal. The controller is operatively connected to the injection device so that individual eggs are injected based on the data collected by the light measuring system; injection occurs only where the data from the light measuring system indicates that the egg is fertile.

One embodiment of a device for the classification of eggs as suitable for injection, and the selective injection of suitable eggs, is schematically illustrated in FIG. 4. A conveyor 50 is configured to move an egg flat 51 (direction of travel indicated by arrow) past a light measuring system 52 designed to classify eggs as suitable or non-suitable. The light measuring system comprises a plurality of light emitters and associated light detectors configured so that light travels through each egg and is detected. Transmission of light through an egg is measured by a light detector, which is operatively connected to a controller 41. A signal is generated by the light detector that indicates whether the egg is suitable or non-suitable; the signal is transmitted to and received by the controller 41. The controller is operatively connected to an injection device comprising an injection head 54 and a fluid delivery system. The injection head comprises a plurality of needles; each needle is aligned with one compartment of the egg flat (i.e., is aligned with the egg contained therein). The fluid delivery system is in fluid communication with a reservoir containing treatment substance (not shown in FIG. 4) and is in fluid communication with an injection needle. The controller generates and transmits to the injection device a signal so that treatment substance is delivered in ovo only to those eggs identified as suitable for injection. Fluid pump 55 may be provided and carried by frame 56.

A top view of an array of fluid pump assemblies for use with a fluid delivery system is illustrated in FIG. 5, with the fluid pump assembly being generally designated 110. The fluid pump assemblies 110 may be advantageously used with injection devices and injection head 54. Each fluid pump assembly 110 may include a fluid channel 120 that interconnects a select valve portion 136, an outlet valve portion 140, a diaphragm valve portion 142, and an input valve portion 144. The fluid pump assembly 110 may be optimally configured for pumping fluids such as one or more fluids for injection into eggs as provided herein.

Figure 6:
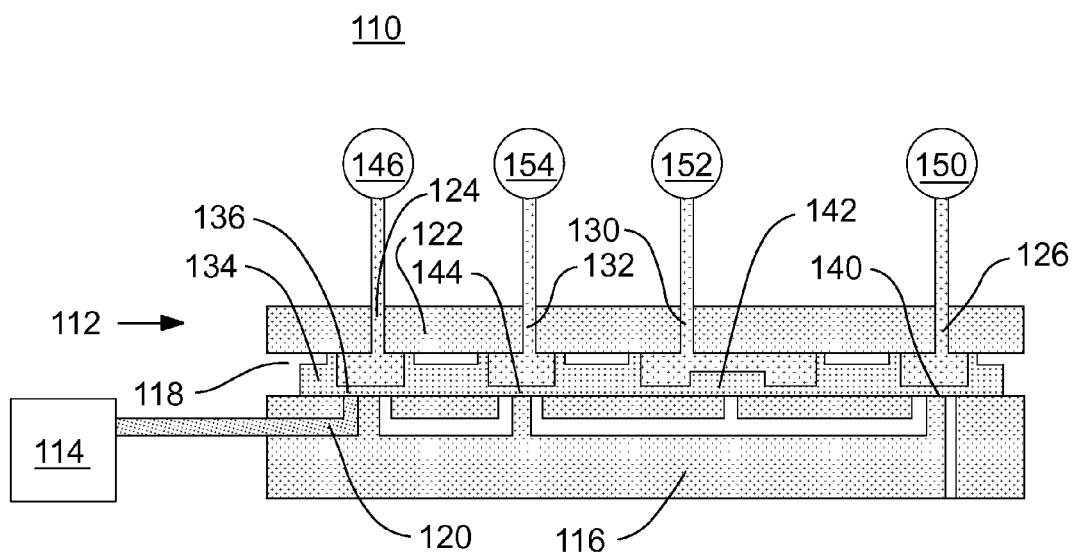

As illustrated more closely in FIG. 6, the pump assembly 110 includes a fluid pump 112 that is in communication with a fluid reservoir 114. The fluid reservoir 114 may include, for example, treatment substance fluids to be injected into an egg. The fluid pump 112 may include a first panel 116. The first panel 116 may be formed of a metal, polymer, composite or similar material. The first panel 116 may define a fluid channel 120 therein. The fluid channel 120 may be configured as illustrated, or may take on any other appropriate configurations. The fluid channel 120 may be configured to receive a fluid treatment substance from the fluid reservoir 114.

The fluid pump 112 may include a second panel 122 spaced-apart and opposing the first panel 116 and defining a chamber 118 therebetween. The second panel 122 may define a select valve channel 124 that extends into the chamber 118 and is configured for supplying a pressure source thereto. The pressure source may be any of a desired pressure source, including a high, low, or vacuum pressure In one or more embodiments, the vacuum may be between 300 and 950 millibars. In one or more embodiments, the vacuum may be between 600 and 700 millibars. The second panel 122 may define an outlet valve channel 126 that is downstream from the select valve channel 124 and extends into the chamber 118 and is configured for supplying a pressure source thereto. The second panel 122 may define a diaphragm valve channel 130 between the select valve channel 124 and the outlet valve channel 126 and that extends into the chamber 118 and is configured for supplying a pressure source thereto. The second panel 122 may define an input valve channel 132 between the select valve channel 124 and the diaphragm valve channel 130 and that extends into the chamber 118 and is configured for supplying a pressure source thereto.

A resilient membrane 134 is provided and configured for being received in the chamber 118. The resilient membrane 134 is in communication with the fluid channel 120 defined in the first panel 116 for directing flow of fluid therethrough. The resilient membrane 134 is configured for allowing selective flowthrough of fluid through the fluid channel 120. The resilient membrane 134 may define a select valve portion 136 that is individually controllable. The select valve portion 136 is in communication with select valve channel 124 defined in the second panel 122. The resilient membrane 134 may define an outlet valve portion 140 that is in communication with outlet valve channel 126 defined in the second panel 122. The resilient membrane 134 may define a diaphragm valve portion 142 that is in communication with diaphragm valve channel 130. The resilient membrane 134 may define an input valve portion 144 that is in communication with input valve channel 132. The resilient membrane 134 is illustrated as a one-piece unit in which each of select valve portion 136, outlet valve portion 140, diaphragm valve portion 142, and input valve portion 144 are interconnected, while, in other embodiments, one or more respective portions may be disjointed.

The fluid pump assembly 110 may further include a select valve actuator 146 that is in fluid communication with the select valve channel 124 for control of the select valve portion 136. Select valve actuator 146 may be operatively coupled to one or more devices for determining viability of a respective egg. In this manner, the select valve actuator 146 may actuate open when an egg is determined viable, or select closed when an egg is determined unviable, thereby saving the substance treatment for a later application.

An outlet valve actuator 150 may be in fluid communication with the outlet valve channel 126 for control of the outlet valve portion 140. A diaphragm actuator 152 may be in fluid communication with the diaphragm valve channel 130 for control of the diaphragm valve portion 142. An input valve actuator 154 may be in fluid communication with the input valve channel 132 for control of the input valve portion 144.

The substance treatment dosings provided by the fluid pump assembly 110 may be oil-based. These oil-based dosings require large pressures to pump the dosing through the pump assembly 110, particularly when the pump channels are relatively small. For relatively small pump channels, the force due to surface tension of the oil-based dosing traveling about the channel becomes a large component compared to the surface area available for pressurizing (i.e., the cross-sectional area of the channel). Due to the high pressures required, diaphragm actuator 152 and input valve actuator 154 may be high pressure actuators. In one or more embodiments, each of the diaphragm actuator 152 and input valve actuator 154 may be actuators configured for actuating at pressures as great as 300 pounds per square inch. Alternatively, the pressures may be as great as 200 pounds per square inch. Actuators 146 and 150 may be low pressure actuators configured for operating below about 30 pounds per square inch. One or more manifolds may be utilized upstream of the pump assembly 110 to further reduce the number of actuators required for operation. In this manner, each pump assembly 110 may have an individually controlled select valve actuator 146, but may share a commonly controlled outlet valve actuator 150, diaphragm actuator 152, and input valve actuator 154, respectively. As used herein, commonly controlled may mean that each commonly controlled valve is actuated by one actuation, whereas, selectively controlled may mean that each valve portion is controlled by an individual actuator. In this manner, an array of pump assemblies 110 could share one outlet valve actuator 150 and one diaphragm valve actuator 152, thereby reducing costs associated with a fluid dispensing system that requires individual actuators for each pump assembly. Actuators may be solenoid valves or any other appropriately configured actuating device.

Sequential operational views of the fluid pump assembly 110 are illustrated in FIGS. 6 through 11. As illustrated in FIG. 6, fluid has not been allowed downstream of the select valve portion 136. In FIG. 6, each of the select valve portion 136 and outlet valve portion 140 are under low pressure. Each of diaphragm valve portion 142 and input valve portion 144 are under high pressure.

Figure 7:
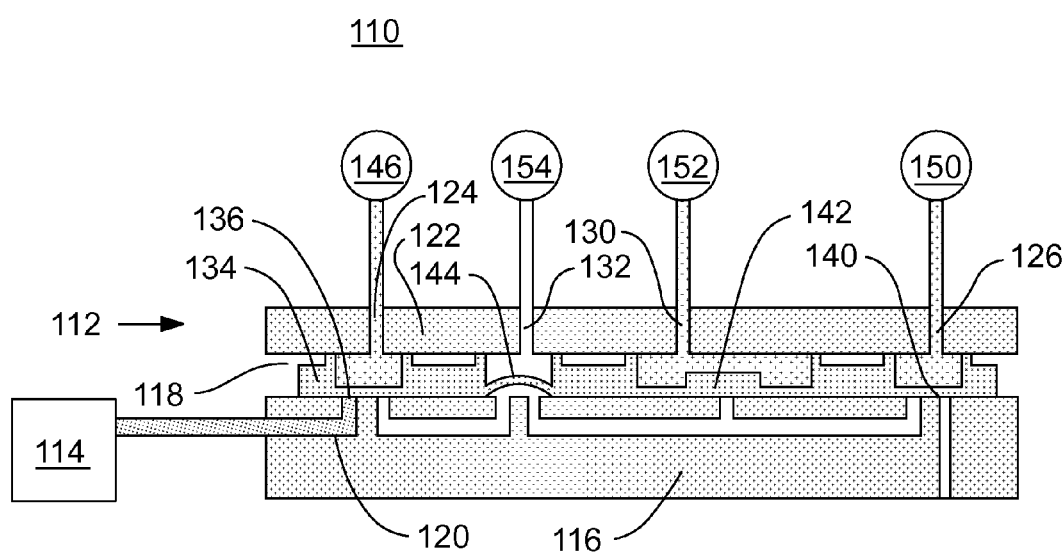

As illustrated in FIG. 7, input valve portion 144 is placed under vacuum which thereby imparts an upward deflection of the input valve portion 144 towards the second panel 122 to thereby open the input valve portion 144. This creates a vacuum pressure downstream of the channel 120 downstream of the select valve portion 136. Select valve portion 136 and outlet valve portion 140 remain at low pressure while diaphragm portion 142 remains at high pressure.

Figure 8:
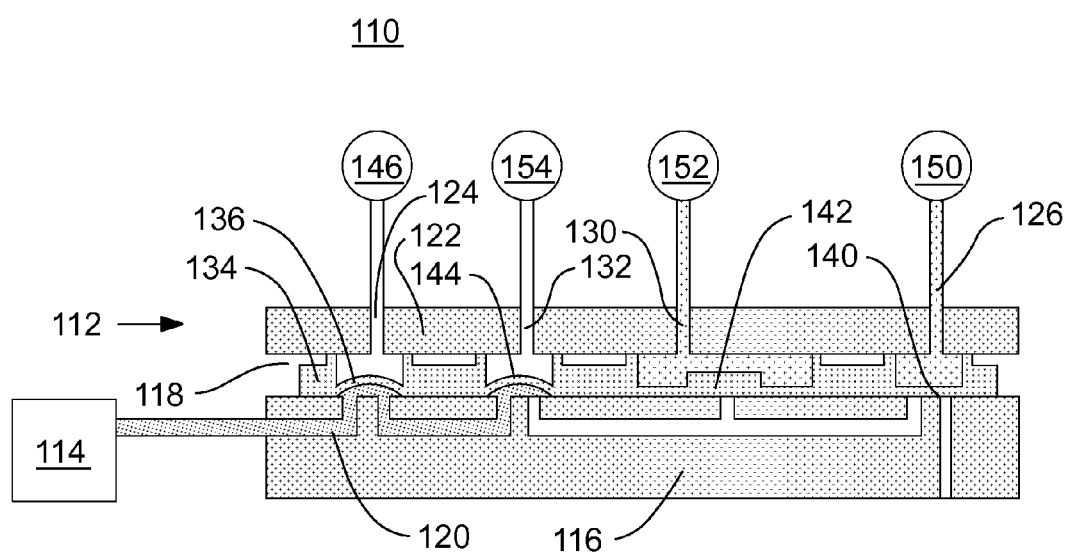

As illustrated in FIG. 8, select valve portion 136 is placed under vacuum which thereby imparts an upward deflection of the select valve portion 136 towards the second panel 122 to thereby open the select valve portion 136. This creates additional vacuum pressure within channel 120, and, with the select valve portion 136 in the open position, allows for flow of treatment fluids within channel 120 towards the input valve portion 144. Diaphragm valve portion 142 remains under high pressure and outlet valve portion 140 remains under low pressure.

Figure 9:
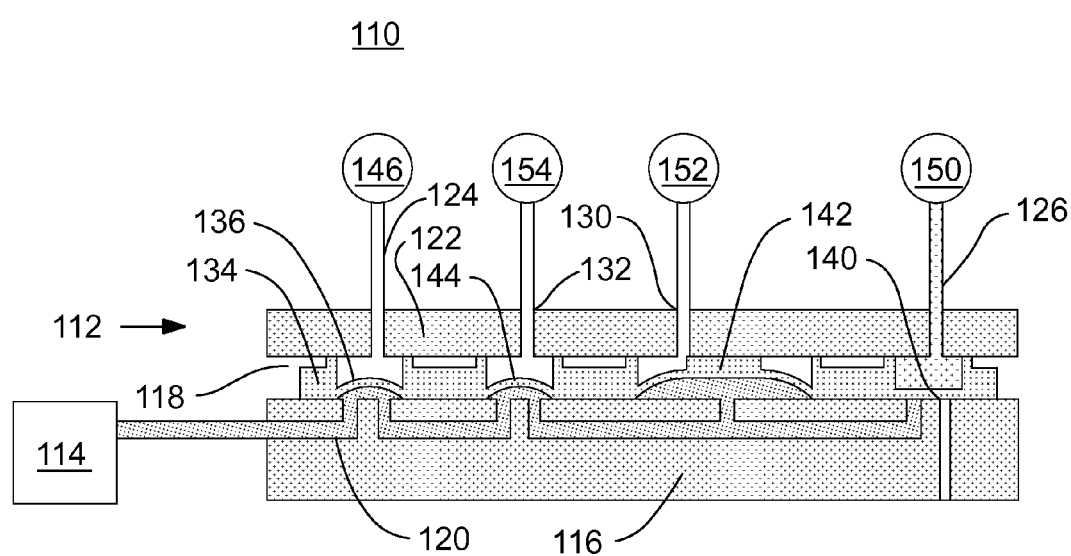

As illustrated in FIG. 9, diaphragm valve portion 142 is placed under a high pressure vacuum which thereby imparts an upward deflection of the diaphragm valve portion 142 towards to second panel to thereby open the diaphragm valve portion 142. This occurs while select valve portion 136 and input valve portion 144 are also under vacuum. Fluid channel 120 is then pressurized due to the displacement of each of select valve portion 136, diaphragm valve portion 142, and input valve portion 144, causing treatment fluids to flow up to the position where the outlet valve portion 140 has closed the channel. The outlet valve portion 140 remains under low pressure. The diaphragm valve portion 142 is sized such that a considerable volume is displaced with displacement of the diaphragm valve portion 142. Accordingly, diaphragm valve portion 142 may be adjusted in configuration in order to determine appropriate dosing amounts.

Figure 10:
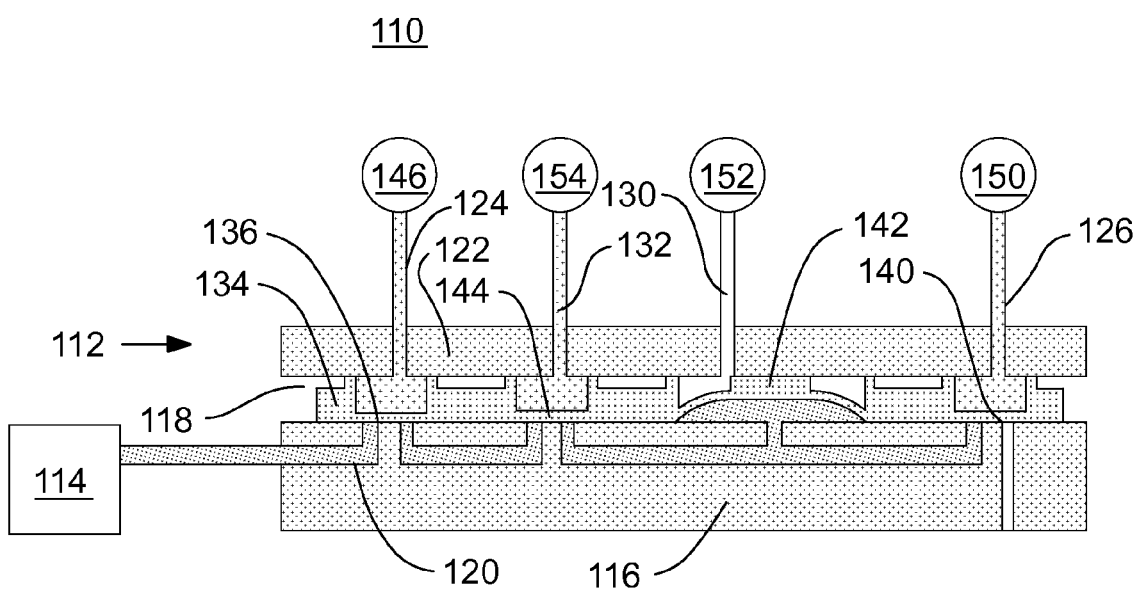

As illustrated in FIG. 10, the vacuum on select valve portion 136 and input valve portion 144 is discontinued and low pressure and high pressure, respectively, are applied, causing each of the select valve portion 136 and input valve portion 144 to return to their biased, closed state, thereby closing fluid channel 120 at each of the select valve portion 136 and input valve portion 144. The diaphragm valve portion 142 continues to be under vacuum and therefore open. High pressure may be applied to the input valve portion 144 to create a sufficiently strong seal so that high pressure caused by closing movement of the diaphragm valve portion 144 does not force the input valve portion 144 to open and cause upstream flow of dosing fluids.

Figure 11:
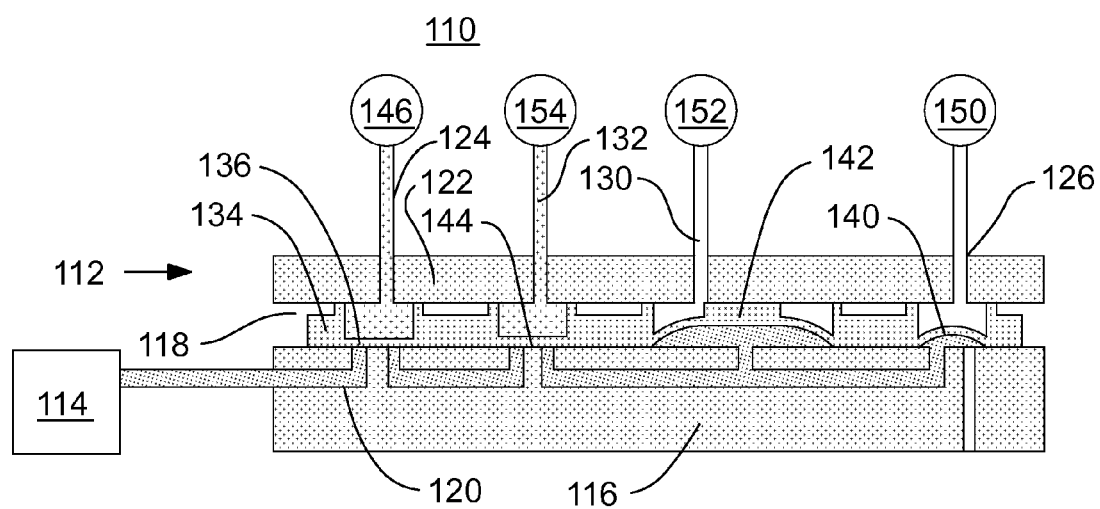

As illustrated in FIG. 11, the outlet valve portion 140 is placed under vacuum which thereby imparts an upward deflection of the outlet valve portion 140 towards to second panel to thereby open the diaphragm valve portion 140. This occurs while the diaphragm valve 142 is also under vacuum. Input valve portion 144 remains under high pressure and select valve portion 136 remains under low pressure.

Figure 12:
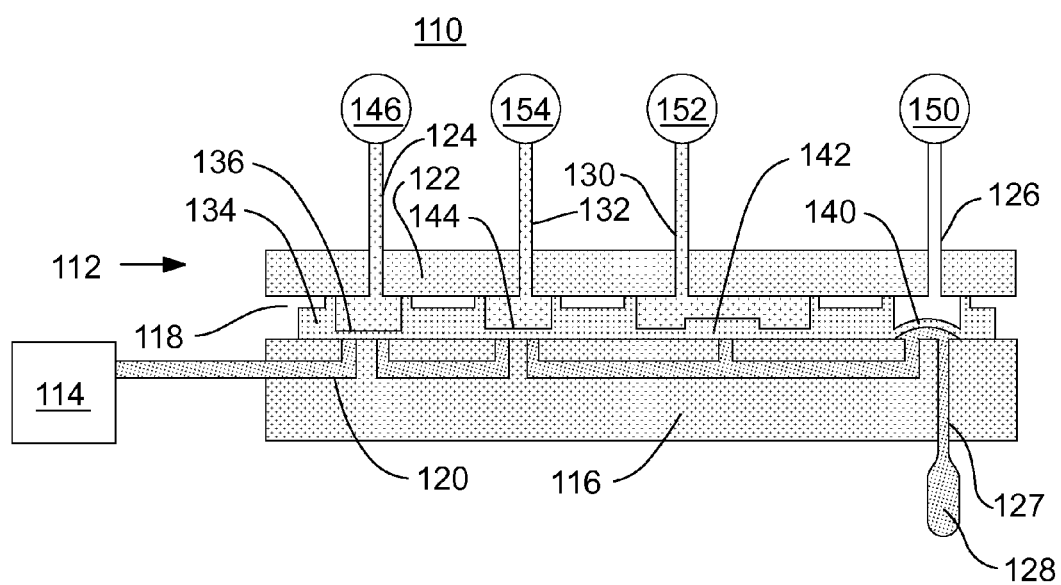

As illustrated in FIG. 12, the vacuum on the diaphragm valve portion 142 is discontinued and a high pressure is applied, causing the diaphragm valve portion 142 to return to the biased, closed state, thereby forcing fluid within the chamber 118 about the diaphragm valve portion 142 into the fluid channel 120. This causes a portion of fluid to exit a dispensing end 127 of the fluid channel 120. The limited volume displacement caused my actuation of the fluid pump assembly 110 in FIG. 12, combined with the surface tension of fluid may cause a droplet of fluid treatment 128 to form and exit the fluid channel 120. This droplet of fluid treatment 128 is representative of one dosing unit that may be provided, for example, for use in an in ovo process as disclosed herein. Dispensing end 127 may be, for example, an injection needle as illustrated in FIG. 1. The outlet valve portion 150 is then closed by application of low pressure, and the pump pressure begins again.

Pressure and vacuum are delivered to each of the select valve portion 136, outlet valve portion 140, diaphragm valve portion 142, and input valve portion 144 by a pressure and/or vacuum source that actuation of which is controlled by respective select valve actuator 146, outlet valve actuator 150, diaphragm valve actuator 152, and input valve actuator 154. Each of the respective actuators may be individually controlled, or, alternatively, a common control system may be employed in which one or more solenoid-type valves utilize a manifold system to control each respective actuator.

One or more embodiments of a valve portion are illustrated in FIG. 13. As illustrated, one or more alternate designs are presented for select valve portion 144, though the design may be equally applicable for diaphragm valve portion 142. The select valve portion 244 is configured to define boss portion 248, which may be, as illustrated, a raised portion extending towards the second panel 122. The boss portion 248 is configured for providing an area of increased thickness and rigidity such that, when high pressure is applied to the select valve portion 244 via activation of the select valve actuator 154 thereby forcing the valve portion 244 into contact with panel 116, a portion of the select valve actuator 154 is not pressed into the portion of the fluid channel 120 that is exposed by the panel 116. Without the boss portion 248, the valve portion 244 may be forced down into channel 120 by high pressure, possibly rupturing, tearing, or otherwise damaging the valve portion 144. As illustrated, two boss portions 248 are provided in a spaced-apart arrangement to cover each channel opening, while also providing sufficient flexibility for the diaphragm to move between the open and closed positions.

In one or more instances, one or more valve portions may be advantageously configured to withstand a high pressure caused by, for example, a pressure from an upstream valve portion closing. For example, the outlet valve 140 may be under high pressures when it is in the closed state and the diaphragm valve 142 is moving from the open to the closed position, thereby displacing high pressure dosing fluids downstream towards the outlet valve 140. This high pressure can cause upward deflection of the outlet valve 140 and, in some instances, non-resilient stretching or tearing thereof.

An outlet valve portion 340 according to one or more embodiments is illustrated in FIG. 14 that advantageously addresses this issue. The outlet valve portion 340 is initially biased towards the second panel 122 in the open position. A first boss portion 348 is provided and configured for engaging the portion of the fluid channel 120 upstream of outlet valve portion 340. A second boss portion 358 is provided and configured for providing an area of increased thickness to prevent a portion of the outlet valve portion 340 from entering the outlet valve channel 126 in a manner similar to that provided for boss portion 248 in FIG. 13. As illustrated in FIG. 14, the outlet valve portion 340 closes under pressure by engagement of the boss portion 340 against the upstream fluid channel 120. The one or more configurations illustrated in FIG. 13 advantageously address the issues of upstream high pressure induced stretching and tearing of the outlet valve portion 340 by limiting the amount of travel that the outlet valve portion 340 undergoes during opening and closing. This can be attributed to the relatively large height of boss portion 348.

A perspective view of a fluid dispensing system is illustrated in FIG. 15. The dispensing system includes an array of fluid pump assemblies 110 that are in communication with channels connecting to fluid reservoir 114. A control system may be connected with blocks 160 and may be provided for communicating commands to each fluid pump assembly 110, such as, for example, to actuate a select valve upon determining viability of an egg.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A fluid delivery system, comprising:
   a plurality of fluid pumps adapted for fluid communication with a fluid reservoir, each fluid pump comprising:
      a fluid channel configured to receive a fluid substance from the fluid reservoir;
      a select valve disposed along the fluid channel and being individually controllable;
      an outlet valve disposed along the fluid channel downstream from the select valve;
      a diaphragm valve disposed along the fluid channel between the select valve and the outlet valve; and
      an input valve disposed along the fluid channel between the select valve and the diaphragm valve;
   a plurality of select valve actuators in fluid communication with the select valves for individual pneumatic control thereof;
   an outlet valve actuator in fluid communication with the outlet valves for commonly controlling pneumatic operation thereof;
   a diaphragm actuator in fluid communication with the diaphragm valves for commonly controlling pneumatic operation thereof;
   an input valve actuator in fluid communication with the input valves for commonly controlling pneumatic operation thereof; and
   a controller operatively connected to the plurality of select valve actuators, the controller configured to:
      receive a signal including data identifying avian eggs suitable for fluid injection;
      generate a selective injection signal based on the data; and
      communicate the selective injection signal to the plurality of select valve actuators to selectively actuate the select valve actuators for fluid injection,
         wherein the select valve actuators, the outlet valve actuator, the diaphragm actuator, and the input valve actuator are configured to control their respective valves by switching between positive air pressure and vacuum, and
         wherein the select valve actuators and the outlet valve actuator are configured to pneumatically control the select valves and the outlet valves at a low pressure of less than about 30 psi (206 KPa), and further wherein the input valve actuator and the diaphragm actuator are configured to pneumatically control the input valves and diaphragm valves at a high pressure of more than about 200 psi (1378 KPa).

2. A fluid delivery system according to claim 1, further comprising a dispensing device in fluid communication with the fluid channel downstream from the outlet valve.

3. A fluid delivery system according to claim 1, wherein the select valve actuators and the outlet valve actuator are low pressure solenoid actuators, and further wherein the input valve actuator and the diaphragm actuator are high pressure solenoid actuators.

* * * * *